US012589187B2

(12) United States Patent
Wang et al.

(10) Patent No.: US 12,589,187 B2
(45) Date of Patent: Mar. 31, 2026

(54) VALVE MATERIAL WITH COMBINED ANTI-CLOTTING AND ANTI-CALCIFICATION PROPERTIES AND PREPARATION METHOD

(71) Applicant: JILIN VENUS HAOYUE MEDICAL LIMITED, Jilin (CN)

(72) Inventors: Yunbing Wang, Changchun City (CN); Li Yang, Changchun City (CN); Rifang Luo, Changchun City (CN); Linhua Li, Changchun City (CN)

(73) Assignee: Jilin Venus Haoyue Medical Limited, Jilin (CN)

( * ) Notice: Subject to any disclaimer, the term of this patent is extended or adjusted under 35 U.S.C. 154(b) by 792 days.

(21) Appl. No.: 18/000,374

(22) PCT Filed: Jun. 15, 2021

(86) PCT No.: PCT/CN2021/100181
§ 371 (c)(1),
(2) Date: Nov. 30, 2022

(87) PCT Pub. No.: WO2021/254346
PCT Pub. Date: Dec. 23, 2021

(65) Prior Publication Data
US 2023/0218803 A1 Jul. 13, 2023

(30) Foreign Application Priority Data
Jun. 15, 2020 (CN) .......................... 202010541893.6

(51) Int. Cl.
*A61L 27/36* (2006.01)
*C12N 5/071* (2010.01)

(52) U.S. Cl.
CPC ....... *A61L 27/3687* (2013.01); *A61L 27/3625* (2013.01); *A61L 27/3629* (2013.01); *C12N 5/0697* (2013.01); *A61L 2300/236* (2013.01); *A61L 2300/252* (2013.01); *A61L 2300/418* (2013.01); *A61L 2300/42* (2013.01)

(58) Field of Classification Search
CPC ............. A61L 27/3687; A61L 27/3625; A61L 27/3629; A61L 2300/236; A61L 2300/252; A61L 2300/418; A61L 2300/42; A61L 27/3641; A61L 2400/02; A61L 2430/20; A61L 27/507; A61L 27/54; A61L 33/0011; A61L 33/0041; A61L 33/0082; A61L 33/08; A61L 33/128; A61L 27/3604; A61L 2300/232; A61L 2400/18; A61L 2430/40; C12N 5/0697
See application file for complete search history.

(56) References Cited

U.S. PATENT DOCUMENTS 5,645,587 A 7/1997 Jyotirmay et al.
9,795,573 B2 * 10/2017 Vyavahare ............. A61K 31/15

FOREIGN PATENT DOCUMENTS

| CN | 101678152 A | 3/2010 | |
| CN | 109260517 A | 1/2019 | |
| CN | 111658824 A | 9/2020 | |
| JP | 4512370 B2 * | 7/2010 | ............. A01N 1/128 |

OTHER PUBLICATIONS

Girardot Jean-Marie et al., machine translation of JP-4512370-B2, 24 pages. (Year: 2010).*
WIPO, China International Search Authority, International Search Report (with English Translation) and Written Opinion mailed Aug. 30, 2021 in International Patent Application No. PCT/CN2021/100181, 12 pages.

* cited by examiner

*Primary Examiner* — Aaron J Kosar

(57) ABSTRACT

The present invention provides a valve material having synergistic anti-coagulation and anti-calcification functions and a preparation method therefor. The preparation method comprises the following steps: performing glutaraldehyde cross-linking treatment on an animal-derived biological valve material; immersing the treated valve material in a blocking solution containing an amine compound for 0.5-6 h, thereby blocking the remaining aldehyde groups after glutaraldehyde cross-linking; then placing the valve material into a reaction solution containing an anticoagulant and a cross-linking agent, and performing cross-linking treatment for 6-24 h at 4° C.-37° C.; and finally washing and obtaining the valve material, and storing the valve material in a mixed solvent of glutaraldehyde or isopropyl alcohol/glycerol. The method can effectively solve the problem of calcification and thrombosis caused by residual aldehyde groups in a valve material prepared by the existing method. The valve material prepared by the present method can be used as a valve material required for aortic valve, pulmonary valve, venous valve, mitral valve and tricuspid valve replacement.

14 Claims, 2 Drawing Sheets

VALVE MATERIAL WITH COMBINED ANTI-CLOTTING AND ANTI-CALCIFICATION PROPERTIES AND PREPARATION METHOD

RELATED APPLICATIONS

This application is the U.S. National Phase of and claims priority to International Patent Application No. PCT/CN2021/100181, International Filing Date Jun. 15, 2021, entitled *Valve Material With Combined Anti-Clotting And Anti-Calcification Properties And Preparation Method Therefor*, which claims benefit of Chines patent application Ser. No. 20/201,0541893.6 filed Jun. 15, 2020; both of which are incorporated herein by reference in their entireties.

TECHNICAL FIELD

The invention belongs to the technical field of modifications to biomedical materials and medical devices, in particular to valve materials with combined anti-clotting and anti-calcification properties and preparation methods therefor. The valve materials prepared according to the inventive method can be used as valve materials for replacement of aortic valve, pulmonary valve, venous valve, mitral valve and tricuspid valve.

BACKGROUND

Transcatheter valve therapy is becoming the mainstream in valve replacement, and the relative technologies include aortic valve, pulmonary valve, mitral valve, tricuspid valve and venous valve replacement. Currently, the valve materials used in interventional procedure are mainly xenograft valve materials, from porcine pericardium, bovine pericardium, small intestinal submucosa and swim bladder and the like. The mechanical strength and service life of the animal derived valve materials can be improved by chemically crosslinking. Commercialized crosslinking methods are mainly induced through glutaraldehyde. The porcine pericardium and bovine pericardium cross-linked with glutaraldehyde have been widely used in the market.

Interventional valve replacement has special requirements for biological valve materials, including mechanical properties, heat shrinkage temperature, hydrodynamics, anti-calcification properties, anti-clotting properties and so on, in which the anti-calcification property is necessary for most valve materials and also ensures the service life of the valves, while the anti-clotting property is particularly required by venous and pulmonary valve materials as venous and pulmonary valves involve complex hemodynamic environment, wherein the circulating blood involves venous blood with slow flow rate that is easy to clot. Despite the disadvantages of glutaraldehyde cross-linked valves, such as calcification, cytotoxicity and thrombotic risk caused by aldehyde residues, the commercialized biovalves are still mainly cross-linked by glutaraldehyde. Many new cross-linking methods are expected to replace glutaraldehyde. However, due to the challenges of valve sterilization, detoxification and preservation, the new cross-linking methods are far way from being commercialized. Thus, there is a need for pulmonary artery/venous valve materials with excellent anti-clotting and anti-calcification properties in clinical practice, with great value in clinical practice and market.

SUMMARY

In view of the above problems in the prior art, the present invention provides a valve material having combined anti-clotting and anti-calcification properties and the preparation method thereof, which can effectively solve the problems that the valve materials prepared in the existing methods are easy to calcification and clot due to the residual aldehyde groups. The valve materials prepared according to the present invention can be used as valve materials for replacement of aortic valve, pulmonary valve, venous valve, mitral valve and tricuspid valve.

For the above objectives, the present invention provides the following technical solution to solve the above technical problems:

A method for preparing a valve material having combined anti-clotting and anti-calcification properties, comprising steps of:

(1) crosslinking an animal-derived biological valve material with glutaraldehyde;

(2) immersing the valve material treated in step (1) into a blocking solution of amino compound;

(3) placing the valve material treated in step (2) into a reaction solution containing an anti-clotting agent and a crosslinking agent; and (4) washing the valve material treated in step (3), thereby obtaining the valve material having combined anti-clotting and anti-calcification properties.

A method for preparing a valve material having combined anti-clotting and anti-calcification properties, comprising steps of:

(1) crosslinking an animal-derived biological valve material with glutaraldehyde so that the valve material can resist decomposition for a long time;

(2) immersing the valve material treated in step (1) into a blocking solution of amino compound for 0.5-6 h, thereby blocking the aldehyde groups residual after glutaraldehyde crosslinking;

(3) placing the valve material treated in step (2) into a reaction solution containing an anti-clotting agent and a crosslinking agent for 6-24 h at a temperature in the range of 4-37° C.; and (4) washing the valve material treated in step (3), thereby obtaining the valve material having combined anti-clotting and anti-calcification properties, and then preserving the valve material in a mixed solvent of glutaraldehyde or isopropanol/glycerol.

Further, the animal-derived biological valve material includes one of porcine pericardium, bovine pericardium and small intestinal submucosa.

Further, the glutaraldehyde in step (1) has a concentration in the range of 0.3 to 3%.

Further, the crosslinking time with glutaraldehyde in step (1) is in the range of 24-96 h, and the crosslinking pH value is in the range of 6-9.

Further, in step (1), the concentration of glutaraldehyde is in the range of 0.3%-3%, the crosslinking time is in the range of 24-96 h, and the crosslinking pH value is in the range of 6-9.

Further, the concentration of glutaraldehyde in step (1) is 1%, the crosslinking time is 72 h, and the crosslinking pH value is 7.

Further, the crosslinking with glutaraldehyde in step (1) includes one-step crosslinking, multi-step crosslinking and concentration gradient crosslinking, and the crosslinking solvent is water, PBS or other salt ion buffers.

Further, the amino compound in step (2) has at least 3 primary amino groups thereon.

Further, the amino compound in step (2) includes one of polyethyleneimine, chitosan, carboxymethyl chitosan, polylysine, polyarginine and hexanediamine, and the concentration of the blocking solution of amino compound is in the range of 0.1-100 mg/mL.

Further, the concentration of the blocking solution of amino compound in step (2) is in the range of 0.1-100 mg/mL.

Further, the concentration of the amino compound in the blocking solution in step (2) is 10 mg/mL.

Further, in step (2), the treated valve material is immersed into the blocking solution of amino compound for 0.5-6 h.

Further, the anti-clotting compound in step (3) includes heparin, heparan sulfate, bivalirudin and hirudin.

Further, the crosslinking agent in step (3) includes one of 1-ethyl-(3-dimethylaminopropyl) carbodiimide hydrochloride, N-hydroxysuccinimide, 1-cyclohexyl-2-morpholinethylcarbodiimide-p-toluenesulfonate, and N, N'-dicyclohexylcarbodiimide.

Further, the solvent in the reaction solution in step (3) includes water, 2-(N-Morpholino)ethanesulfonic acid sodium salt solution, and PBS buffer.

Further, in step (3), the concentration of the anti-clotting agent in the reaction solution is in the range of 0.2 mg/mL-20 mg/mL, and the molar ratio of the anti-clotting agent to the crosslinking agent is in the range of 0.2-5:0.2-2.

Further, the concentration of the cross-linking agent in the reaction solution in step (3) is in the range of 0.1 to 5 mg/mL.

Further, in step (3), the concentration of the anti-clotting agent in the reaction solution is 5 mg/mL, and the molar ratio of the anti-clotting agent to the crosslinking agent is 0.3:2.

A valve material with combined anti-clotting and anti-calcification properties can be prepared by the above method.

The advantages of the present invention are:

A valve material with combined anti-calcification and anti-clotting properties is prepared for pulmonary artery/vein valves by a two-step magnification effect in the valve. The glutaraldehyde cross-linked valve material is a material with fiber orientation and porous structure, with aldehyde groups, carboxyl groups and other groups on the fiber. In the present invention, the magnification effect of the anti-clotting for the valve is realized by means of perfusion of the polyamino compound and fixation of the anti-clotting compound, providing better antithrombotic activity for the pulmonary artery/venous valve material in the complex hemodynamic environment. By introducing the polyamino compound, the residual aldehyde groups are directly blocked by a schiff base reaction between the amino groups of the polyamino compound and the aldehyde groups of the valve material, preventing calcium ions from adhering to the residual aldehyde groups to form calcium salt crystals, improving the anti-calcification ability of the valve material, thereby increasing the service life of the valve. In addition, amido bonds can be formed through dehydration condensation between the carboxyl groups of the anti-clotting agent and the introduced amino groups to realize covalent fixation, thereby improving the anti-clotting effect of the valve.

4

Figure 2:
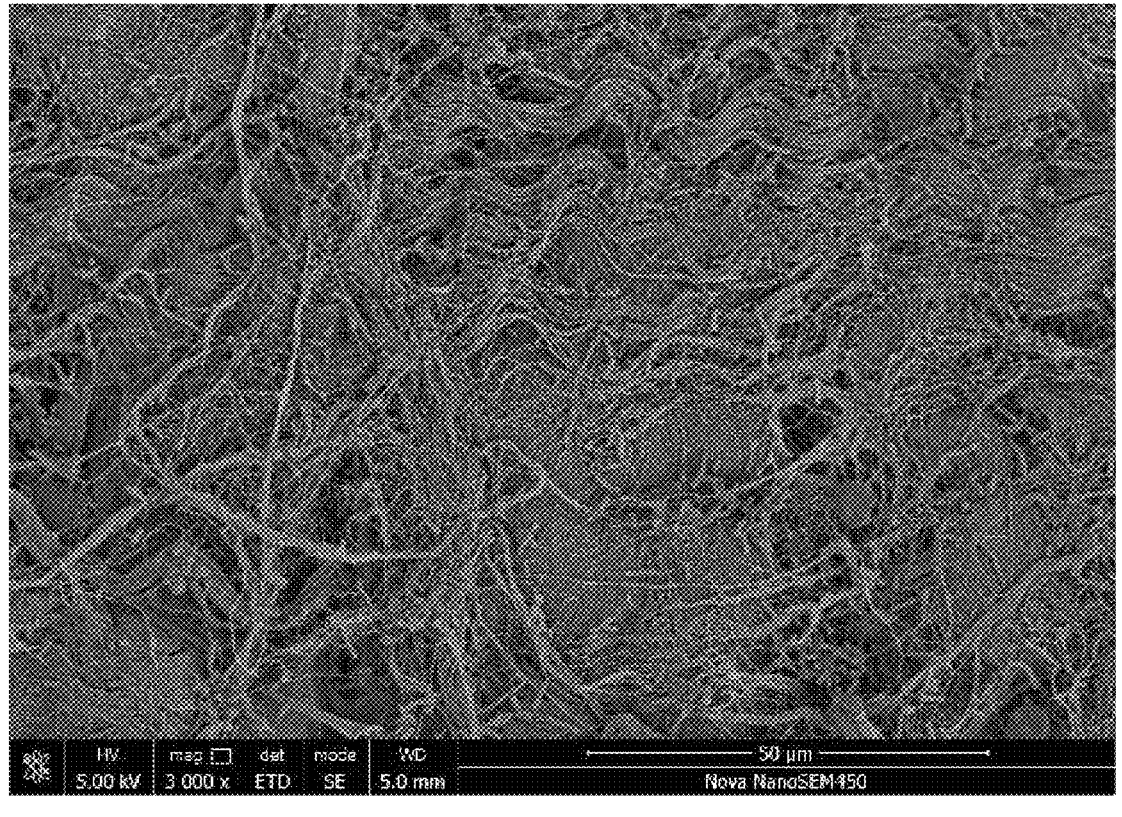

FIG. 2 shows thrombosis on the surface of modified valve material; and

Figure 3:
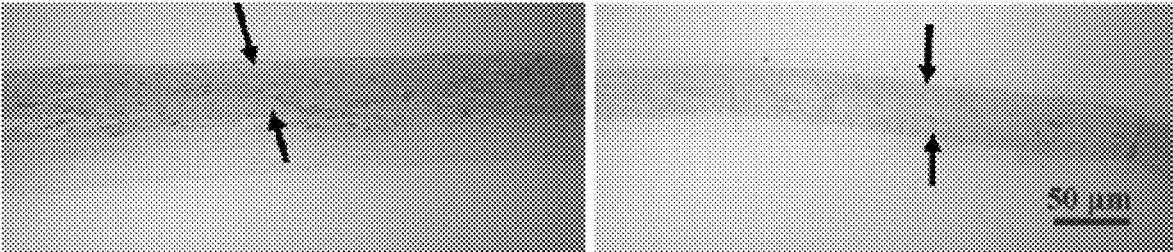

FIG. 3 (left figure) shows calcification of glutaraldehyde cross-linked valve material after subcutaneous implantation for 3 months, and FIG. 3 (right figure) shows calcification of modified valve material after subcutaneous implantation for 3 months.

DESCRIPTION OF THE EMBODIMENTS

The specific embodiments of the present invention will be described in detail with reference to the drawings.

Example 1

A valve material having combined anti-clotting and anti-calcification properties is prepared through the following steps:

(1) Cut a defatted porcine pericardium material into an appropriate size, stretch the material and then immerse it into a glutaraldehyde solution with a concentration of 1% and a pH value of 7, renew the solution after 24 hours, and repeat the treatment for 72 hours;

(2) Immerse the valve material treated in step (1) into a blocking solution (pH value: 7.4) containing polyethyleneimine (10 mg/mL) for 0.5 h at room temperature to block the aldehyde groups residual after glutaraldehyde crosslinking;

(3) Transfer the glutaraldehyde cross-linked valve material obtained in the above step into an IVIES buffer, and add heparin (5 mg/mL) and N, N'-dicyclohexylcarbodiimide (0.5 mg/mL) for cross-linking treatment at a pH value of 5.5 for 24 h; and (4) Wash the valve material obtained after the treatment with the above reaction solution to obtain the desired valve material.

Example 2

A valve material having combined anti-clotting and anti-calcification properties is prepared through the following steps:

(1) Cut a defatted porcine pericardium material into an appropriate size, stretch the material and then immerse it into a glutaraldehyde solution with a concentration of 0.5% and a pH value of 8.5 for 24 hours, and then transfer the material into a glutaraldehyde solution with a concentration of 1% for 48 hours;

(2) Immerse the valve material treated in step (1) into a blocking solution (pH value: 7.4) containing polylysine (5 mg/mL) for 6 h at room temperature to block the aldehyde groups residual after glutaraldehyde crosslinking;

(3) Transfer the glutaraldehyde cross-linked valve material obtained in the above step into a PBS buffer, and add bivalirudin (1 mg/mL) and 1-ethyl-(3-dimethylaminopropyl) carbodiimide hydrochloride (0.3 mg/mL) for cross-linking treatment at 25° C. with a pH value of 6 for 4 h; and (4) Wash the valve material obtained after the treatment with the above reaction solution to obtain the desired valve material.

Example 3

A valve material having combined anti-clotting and anti-calcification properties is prepared through the following steps:

(1) Cut a defatted bovine pericardium material into an appropriate size, stretch the material and then immerse it into a glutaraldehyde solution with a concentration of 1% and a pH value of 6.5 for 24 hours, and then transfer the material into a glutaraldehyde solution with a concentration of 0.5% for 48 hours;

(2) Immerse the valve material treated in step (1) into a blocking solution (pH value: 7.4) containing hexanediamine (4 mg/mL) for 3 h at room temperature to block the aldehyde groups residual after glutaraldehyde crosslinking;

(3) Transfer the glutaraldehyde cross-linked valve material obtained in the above step into a PBS buffer, and add hirudin (2 mg/mL) and 1-ethyl-(3-dimethylaminopropyl) carbodiimide hydrochloride (0.4 mg/mL) for cross-linking treatment at 37° C. with a pH value of 5 for 2 h; and (4) Wash the valve material obtained after the treatment with the above reaction solution to obtain the desired valve material.

Example 4

A valve material having combined anti-clotting and anti-calcification properties is prepared through the following steps:

(1) Peel off and cut a small intestinal submucosa into an appropriate size, stretch the material and then immerse it into a glutaraldehyde solution with a concentration of 1% and a pH value of 8 for 72 hours;

(2) Immerse the valve material into a blocking solution (pH value: 5) containing chitosan (10 mg/mL) for 6 h at room temperature to block the aldehyde groups residual after glutaraldehyde crosslinking;

(3) Transfer the glutaraldehyde cross-linked valve material obtained in the above step into a PBS buffer, and add heparan sulfate (3 mg/mL) and 1-cyclohexyl-2-morpholinethylcarbodiimide-p-toluenesulfonate (0.8 mg/mL) for cross-linking treatment at 20° C. with a pH value of 6.5 for 8 h; and (4) Wash the valve material obtained after the treatment with the above reaction solution to obtain the desired valve material.

Example 5

A valve material having combined anti-clotting and anti-calcification properties is prepared through the following steps:

(1) Cut a defatted porcine pericardium material into an appropriate size, stretch the material and then immerse it into a glutaraldehyde solution with a concentration of 1% for 72 hours;

(2) Immerse the valve material treated in step (1) into a blocking solution (pH value: 7.4) containing polyarginine (5 mg/mL) for 4 h at room temperature to block the aldehyde groups residual after glutaraldehyde crosslinking;

(3) Transfer the glutaraldehyde cross-linked valve material obtained in the above step into 2-(N-Morpholino) ethanesulfonic acid sodium salt buffer, and add heparin (6 mg/mL) and 1-cyclohexyl-2-morpholinethylcarbodiimide-p-toluenesulfonate (1 mg/mL) for cross-linking treatment at 10° C. with a pH value of 5.5 for 20 h; and

(4) Wash the valve material obtained after the treatment with the above reaction solution to obtain the desired valve material.

Test Example

Figure 1:
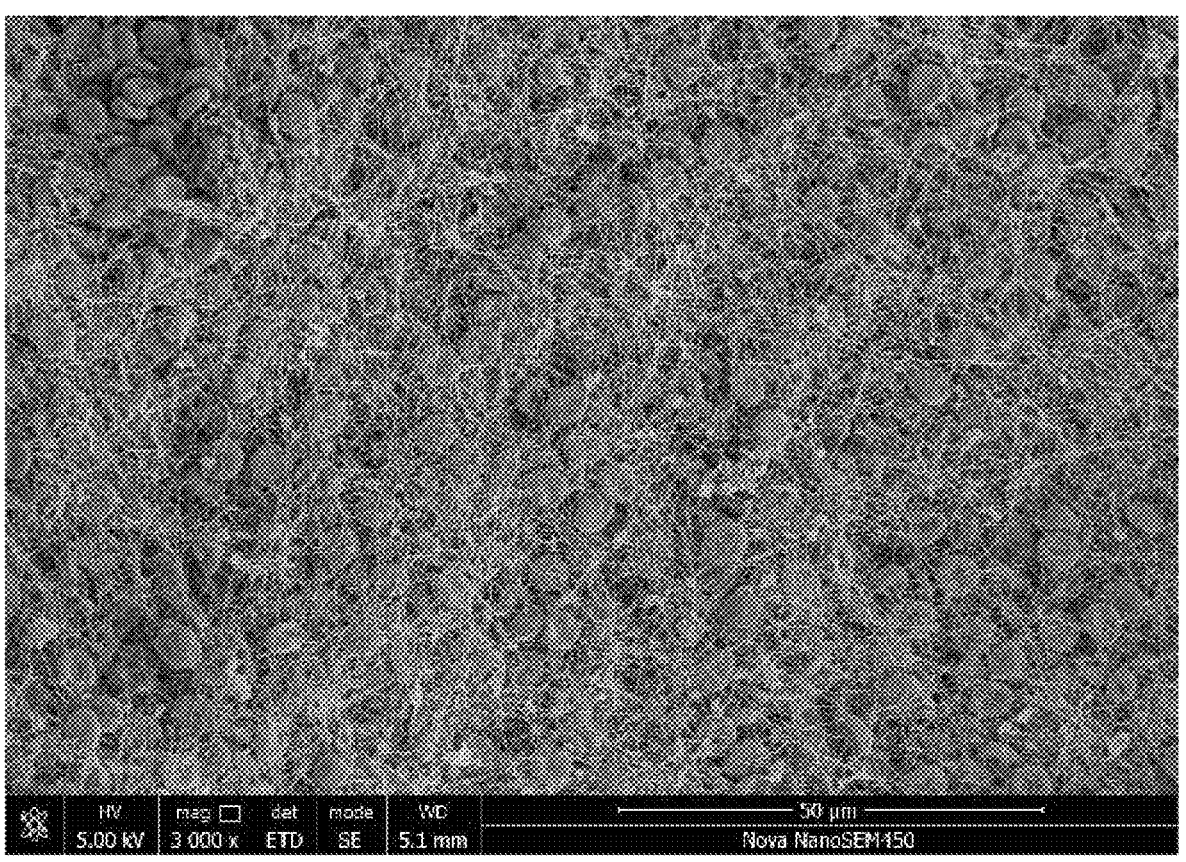
FIG. 1 shows thrombosis on the surface of glutaraldehyde cross-linked valve material.

Taking the valve material prepared in EXAMPLE 1 as an example, the thrombosis on the surface of the glutaraldehyde cross-linked valve material is observed, and then the thrombosis on the surface of the modified valve material is observed after blood circulation test of rabbit ex vivo for 2 hours. The specific results are shown in FIG. 1 and FIG. 2. The glutaraldehyde cross-linked valve material and the modified valve material in EXAMPLE 1 are implanted subcutaneously for 3 months, respectively, and the calcification of the valve materials is observed, as shown in FIG. 3.

As can be seen from FIG. 1, the conventional glutaraldehyde cross-linked valve material without modification is deposited with a large amount of thrombus, red blood cells and a large amount of criss-crossed fibrous. However, FIG. 2 shows that after the anti-clotting modification described in EXAMPLE 1, the surface of the valve material is still smooth without significant thrombosis, proving the excellent blood compatibility and anti-clotting properties of the modified valve material.

As shown in FIG. 3, after 3 months of the subcutaneous implantation and staining with alizarin red, there are significant calcified plaques on the glutaraldehyde cross-linked valve material (left figure), while the modified valve material (right figure) is still smooth without significant thrombosis, which proves the anti-calcification property of the valve material.

What is claimed is:

1. A method for preparing a valve material having combined anti-clotting and anti-calcification properties, comprising steps of:

(1) crosslinking an animal-derived biological valve material with glutaraldehyde;

(2) immersing the valve material treated in step (1) into a blocking solution of amino compound;

(3) placing the valve material treated in step (2) into a reaction solution containing an anti-clotting agent and a crosslinking agent which is at least one selected from a group consisting of 1-ethyl-(3-dimethylaminopropyl) carbodiimide hydrochloride, N-hydroxysuccinimide, 1-cyclohexyl-2-morpholinethylcarbodiimide-p-toluenesulfonate, and N,N'-dicyclohexylcarbodiimide; and (4) washing the valve material treated in step (3), thereby obtaining the valve material having combined anti-clotting and anti-calcification properties.

2. The method for preparing a valve material having combined anti-clotting and anti-calcification properties of claim 1, wherein the amino compound in step (2) has at least three primary amino groups.

3. The method for preparing a valve material having combined anti-clotting and anti-calcification properties of claim 1, wherein the amino compound in step (2) is at least one selected from a group consisting of polyethyleneimine, chitosan, carboxymethyl chitosan, polylysine, polyarginine and hexanediamine.

4. The method for preparing a valve material having combined anti-clotting and anti-calcification properties of claim 1, wherein the anti-clotting agent in step (3) is at least one selected from a group consisting of heparin, heparan sulfate, bivalirudin and hirudin.

5. The method for preparing a valve material having combined anti-clotting and anti-calcification properties of claim 1, wherein the blocking solution of amino compound in step (2) has a concentration in a range of 0.1-100 mg/mL.

6. The method for preparing a valve material having combined anti-clotting and anti-calcification properties of claim 1, further comprising immersing the treated valve material into the blocking solution of amino compound for 0.5-6 h in step (2).

7. The method for preparing a valve material having combined anti-clotting and anti-calcification properties of claim 1, further comprising placing the valve material treated in step (2) into the reaction solution containing the anti-clotting agent and the crosslinking agent for 6-24 h at a temperature in a range of 4-37° C.

8. The method for preparing a valve material having combined anti-clotting and anti-calcification properties of claim 1, wherein the anti-clotting agent in the reaction solution in step (3) has a concentration in a range of 0.2 mg/mL to 20 mg/mL.

9. The method for preparing a valve material having combined anti-clotting and anti-calcification properties of claim 1, wherein a molar ratio of the anti-clotting agent to the crosslinking agent in step (3) is (0.2-5):(0.2-2).

10. The method for preparing a valve material having combined anti-clotting and anti-calcification properties of claim 1, wherein a solvent in the reaction solution in step (3) comprising water, 2-(N-morpholino) ethanesulfonic acid sodium salt solution, and PBS buffer.

11. The method for preparing a valve material having combined anti-clotting and anti-calcification properties of claim 1, wherein the glutaraldehyde in step (1) has a concentration in a range of 0.3 to 3%.

12. The method for preparing a valve material having combined anti-clotting and anti-calcification properties of claim 1, further comprising crosslinking the animal-derived biological valve material with glutaraldehyde for 24-96 h at a pH value in a range of 6-9.

13. The method for preparing a valve material having combined anti-clotting and anti-calcification properties of claim 1, wherein the animal-derived biological valve material comprises one of porcine pericardium, bovine pericardium and small intestinal submucosa.

14. A valve material having combined anti-clotting and anti-calcification properties, which is prepared by the method according to claim 1.

\* \* \* \* \*